United States Patent
Klinkhammer

(10) Patent No.: US 7,411,668 B2
(45) Date of Patent: Aug. 12, 2008

(54) LIGHT RETURNING TARGET FOR A PHOTOMETER

(75) Inventor: Gary Klinkhammer, Corvallis, OR (US)

(73) Assignee: Zaps Technologies Incorporated, Corvallis, OR (US)

( * ) Notice: Subject to any disclaimer, the term of this patent is extended or adjusted under 35 U.S.C. 154(b) by 298 days.

(21) Appl. No.: 11/236,177

(22) Filed: Sep. 26, 2005

(65) Prior Publication Data
US 2007/0070333 A1    Mar. 29, 2007

(51) Int. Cl.
*G01J 1/00*    (2006.01)
(52) U.S. Cl. .................................................. 356/213
(58) Field of Classification Search ......... 356/213–236; 359/664
See application file for complete search history.

(56) References Cited

U.S. PATENT DOCUMENTS

| | | | |
|---|---|---|---|
| 3,904,277 A * | 9/1975 | Phillips et al. ......... 235/472.03 |
| 5,304,492 A | 4/1994 | Klinkhammer |
| 5,403,773 A * | 4/1995 | Nitta et al. ...................... 438/7 |
| 5,738,677 A * | 4/1998 | Colvard et al. .................. 606/4 |
| 5,940,564 A * | 8/1999 | Jewell .......................... 385/93 |
| 6,035,664 A * | 3/2000 | Hashizume ..................... 65/36 |
| 6,740,244 B2 | 5/2004 | Baca |
| 6,747,805 B2 * | 6/2004 | Sayag .......................... 359/664 |
| 6,919,019 B2 | 7/2005 | Baca et al. |
| 7,215,479 B1 * | 5/2007 | Bakin .......................... 359/664 |
| 2003/0127520 A1 * | 7/2003 | Aizawa et al. ......... 235/472.03 |

* cited by examiner

*Primary Examiner*—Gregory J Toatley, Jr.
*Assistant Examiner*—Jarreas C Underwood
(74) *Attorney, Agent, or Firm*—Portland Intellectual Property, LLC

(57) ABSTRACT

A light returning target for a photometer. The light returning target comprises a ball lens, and a cradle. The cradle has a hemispherical receptacle in which the lens is intimately received. Preferably, the lens is formed of fused silica, the receptacle is polished sufficiently to reflect, more than it scatters, light, and at least the surface of the receptacle is formed of a material that absorbs, more than it reflects, light.

33 Claims, 2 Drawing Sheets

LIGHT RETURNING TARGET FOR A PHOTOMETER

FIELD OF THE INVENTION

The present invention relates to a light returning target for a photometer. More particularly, the invention relates to such a target in a fiber optic spectrophotometer for measuring absorption, reflection, and fluorescence from impurities in water.

BACKGROUND

There is a need to measure the purity of fluids in many different circumstances. In addition to the familiar examples of monitoring the quality of air and water, chemicals used for industrial processing and laboratory or analytical purposes must meet certain standards of purity. It is particularly important in processes for treating fluids, such as for processing raw water into potable water, or for processing wastewater so that it is safe for release into the environment, to measure purity both before and after the fluid is treated. That is, measuring purity in fluid before it is treated is often desirable to determine how to treat the fluid, and measuring purity at the end of treatment is often necessary as a quality control, or to confirm conformance to regulatory standards.

Devices used for measuring fluid purity in general, and for identifying and quantifying the amount of impurities in particular, commonly use light as a probing mechanism. Such devices are generally referred to as photometers. A specific type of photometer is the spectrophotometer, which permits adjustment of the light frequency (i.e., wavelength), for making measurements at multiple frequencies. The term "spectrophotometer" as used herein includes any photometer, including reflectometers, transmissometers, and nephelometers, adapted for this purpose.

Light that is used to irradiate material may either be reflected by the material, transmitted through the material, or absorbed by the material. Where the light is absorbed by the material, the material may also emit light in response, or fluoresce. In devices used to measure purity, one of three basic measurement methodologies following from these potential interactions of the light with the matter is generally employed. These methodologies measure the parameters absorption, reflectance, and fluorescence and are referred to herein as absorption, reflectance, and fluorescence methodologies. According to the various methodologies, a light detector is disposed with respect to a light transmitter so that the detector is optimally positioned to be responsive to the associated parameter.

For example, for responding to absorption, the detector is typically disposed directly opposite the transmitter, to detect light that is undeflected from its original path; for responding to reflectance, the detector is typically disposed directly adjacent or next to the transmitter, to detect light that is reflected from surfaces; and for responding to fluorescence, the detector is typically disposed at an angle from the transmitter, to detect omnidirectional fluorescent emissions.

However, as can be readily appreciated, in each of the above detector/transmitter configurations, the detector will in general respond to at least one other parameter. In the absorption methodology, the detector response will be affected by both reflectance and fluorescence as well as absorption; in the reflectance methodology, the detector response will be influenced by fluorescence as well as reflectance; and in the fluorescence methodology, the detector will be influenced by reflectance as well as fluorescence.

Accordingly, it is typical in analytical laboratories to pre-process the sample being tested, or to adjust the measurement methodology, to minimize or eliminate responses due to parameters that are not being measured. For example, in the absorption and fluorescence methodologies, the sample can be clarified to eliminate particulates that would introduce reflectance, and in the reflectance and absorption methodologies, the light can be filtered at both the transmitter and the receiver to limit the response to frequencies in which fluorescence is expected.

Testing fluid quality in a laboratory as a control mechanism has serious drawbacks, as explained in the present inventor's U.S. Pat. No. 5,304,492, incorporated by reference herein in its entirety. To solve these problems, the '492 patent discloses an in-situ spectrophotometer having a single transmitter/detector configuration that is indicated as being capable of use for measuring absorption, reflectance, and fluorescence. The device provided for measurement of any the three desired parameters in essentially real-time, in the flow stream of the fluid being tested. The device remains extremely advantageous for measuring a selected one of these different parameters. However, as recognized and explained herein, there is a need for a light returning target for a photometer for measuring more than one of these parameters in the same device.

SUMMARY

A light returning target for a photometer is disclosed herein. The light returning target comprises a substantially spherical lens, and a cradle. The cradle has a matchingly hemispherical receptacle in which the lens is intimately received. Preferably, the lens is formed of fused silica, the surface of the receptacle is polished sufficiently to reflect, more than it scatters, light, and at least the surface of the receptacle is formed of a material that absorbs, more than it reflects, light.

Also disclosed is a photometer comprising the target. The photometer comprises a light source and is adapted to emit light from the light source along a line. The cradle is oriented so that the lens and the cradle together return at least a portion of the light along this line.

Preferably, the photometer further comprises a chamber, a light detector, and a light pipe set including a bifurcated optical fiber for conducting the light from the light source to the chamber and for conducting the light from the chamber to the light detector, the target being disposed inside the chamber.

Further, the photometer preferably includes a flow tube having one or more fluid inlets and one or more fluid outlets providing for fluid flow through the flow tube. The target is disposed within the flow tube, and the flow tube has an interior surface that is smooth relative to the interior surface of the chamber, to help maintain laminar flow around the target.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION OF PREFERRED EMBODIMENTS

As mentioned above, the '492 patent discloses an "in-situ" spectrophotometer that is advantageous for measuring a selected one of the aforementioned absorbance, reflectance, and fluorescence parameters. However, the present inventor has recognized further that it would be desirable to be able to measure a number of these parameters together, using a single "multi-parameter" device. Essentially, it is recognized that, the greater number of the parameters that are measured, the less likely a change in the impurity content of the fluid being tested can escape detection, particularly in a continuously flowing fluid. For example, this capability is especially important in continuous municipal monitoring of water quality, to provide safe and secure supply of drinking water; however, it is desirable when monitoring impurities in any fluid, for any purpose. Accordingly, while preferred embodiments of the invention are particularly adapted for measuring impurities in water, it should be understood that the principles of the invention may be applied to any fluid or use.

Figure 1:
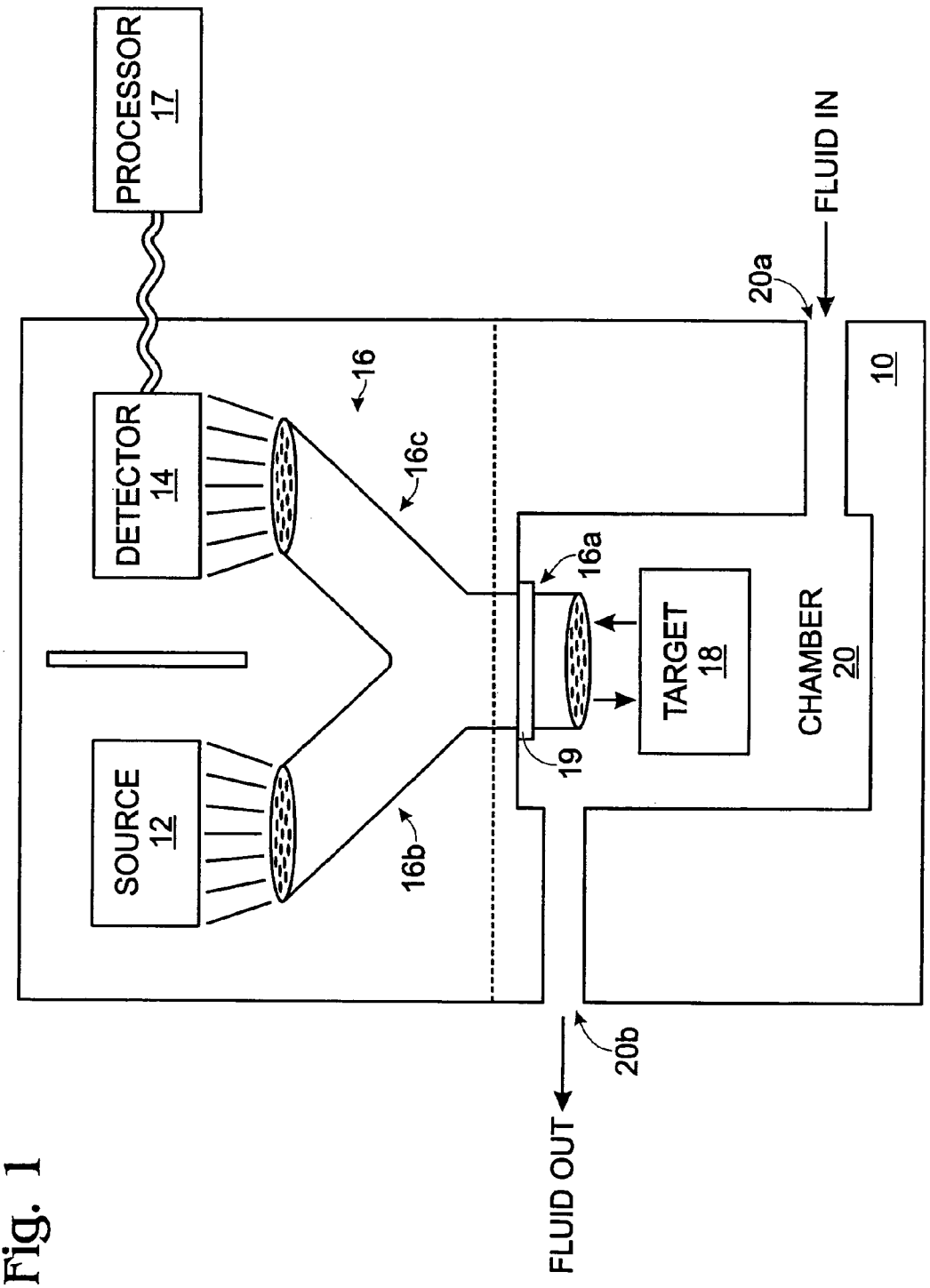
FIG. 1 is a block diagram of a photometer having a light returning target according to the present invention.

Referring to FIG. 1, an impurity measurement device 10 is shown in general form that provides for measuring any combination of the parameters reflectance, absorption, and fluorescence, where it should be understood that all of these parameters may be related to transmission. That is, a beam of light is emitted into a space 20 in the device 10 in which resides the fluid to be tested. The beam of light has a frequency spectrum (which may be a single frequency but which is in general a range of frequencies) and an intensity that is a function of the frequency. This intensity function may be referred to for present purposes as simply representing a quantity of incoming light. Assuming an otherwise optically clear fluid, the light is either absorbed or reflected by impurities in the fluid, or there is no interaction of the light with the impurities and the light is simply transmitted through the fluid. In that regard, it should be noted that fluorescence is a special case of absorption, where the absorbed light is re-emitted at a different frequency instead of being dissipated as heat as is the case with non-fluorescent light absorbing materials. It may also be noted that reflection occurs from solid, or particulate impurities, while absorption may occur in dissolved impurities as well as particulate impurities. In any event, in general, the quantity of light transmitted equals the quantity of light emitted minus the quantities of light that are absorbed and reflected.

The device 10 includes a source 12, a detector 14, a light pipe set 16, and a "target" 18. All except the target 18 may be conventional, such as described in the '492 patent, and preferred embodiments of these components are described below, it being understood that the target 18 may be used with alternative embodiments.

The source 12 is preferably a source of intense white light such as a xenon flash tube, which provides for high intensity by producing the light in pulses. Preferably, the device 10 is adapted as a spectrophotometer, the source emits light in the frequency range of about 200-900 nm, and spectral filters are exchanged such as known in the art to select particular frequencies of the light. However, a frequency adjustable monochromatic light source, either continuous or discontinuous, may be used for the same purpose. As will be readily appreciated by persons of ordinary skill in the art, the use of light characterized by multiple frequencies is important to making multi-parameter measurements; however, the manner in which this is accomplished is not particularly pertinent to the invention and further discussion of this point is therefore omitted.

The detector 14 may be any component or device that is responsive to light intensity, such as a standard photo-multiplier tube, the output of which is amplified and preferably converted to digital form for processing, such as in a remote processor 17, that includes providing a data output for display and/or storage for subsequent use.

The light pipe set 16 provides for two conductive paths (a) conducting light emitted from the source to an interior chamber 20 of the device 10, and (b) conducting light from the chamber 20 to the detector 14. The light pipe set 16 employs optical fibers, e.g., plastic clad fused silica, and is preferably bifurcated as shown in FIG. 1 so that it has a single end 16a that connects to the chamber 20 via a block 19 for conducting light both in and out of the chamber 20, and two separate ends 16b and 16c connecting to the light source and detector, respectively. Employing the single end 16a to connect to the chamber advantageously provides that the detector is able to collect light returned from the chamber at a point that is very close to that at which light is emitted by the source into the chamber, as well as simplifies the physical connections required.

Especially where the device 10 is intended for submersible use, the source 12 and detector 14 are preferably remote from the remainder of the device, separating the device at the indicated dashed line.

Figure 2:
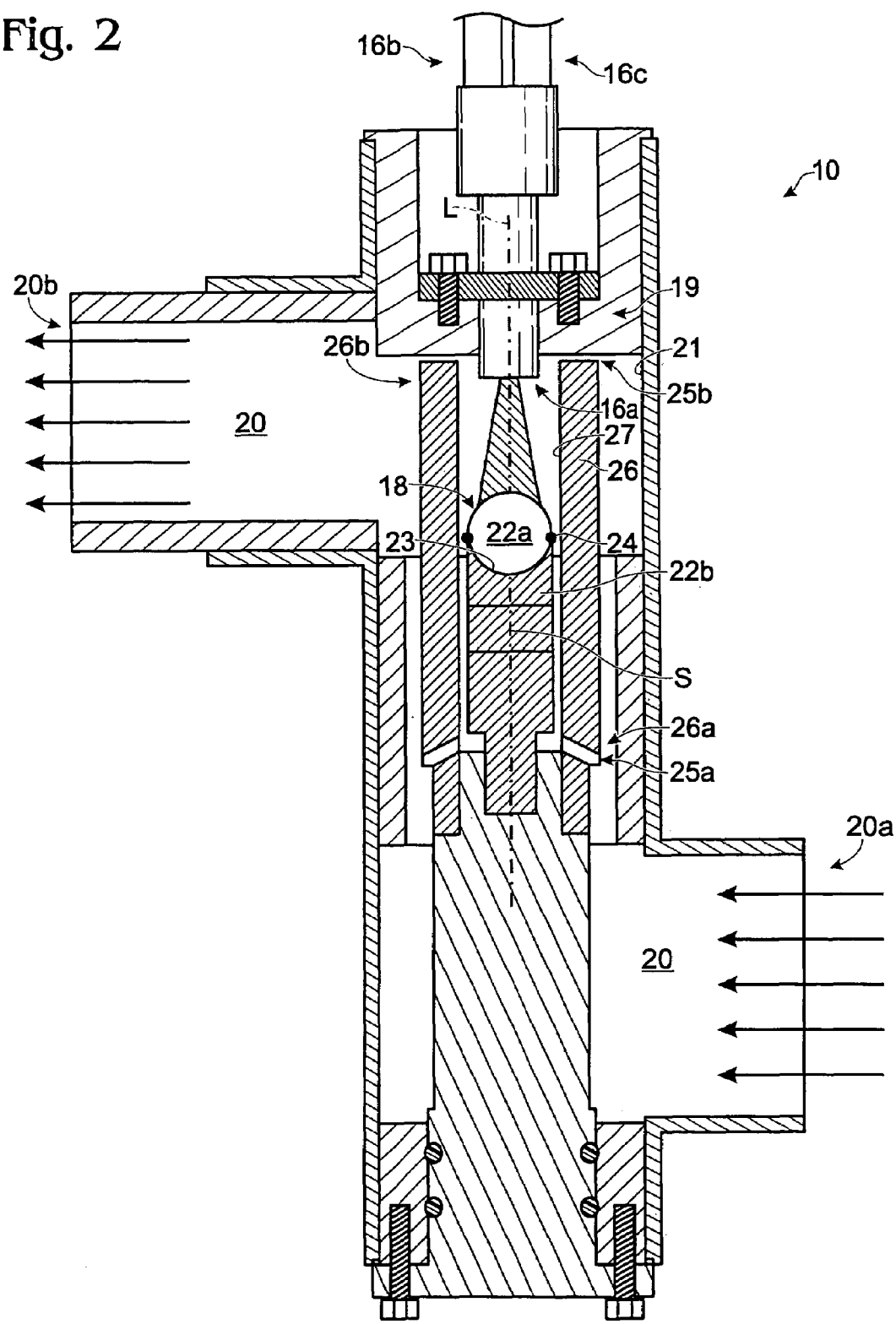
FIG. 2 is a section view of a particular, preferred embodiment of the photometer and light returning target of FIG. 1.

Referring to FIG. 2, the chamber 20 in the preferred embodiment shown is formed by connecting two, 2 inch diameter PVC "T" connectors together, but may be formed in any number of alternative ways. An upper opening of one of the connectors receives the block 19. Respective side openings of the connectors provide for a water inlet 20a and a water outlet 20b. Water flowing through the chamber envelopes the target 18 and the common end of the bifurcated fiber assembly 16a. Light enters the water directly from the end 16a of the fiber bundle.

The target 18 returns the light emitted from the source 12 (FIG. 1) through the end 16a into the water, back into the end 16a and thence to the detector 14 (FIG. 1) in the absence of impurities in the water that would otherwise absorb or reflect the emitted light. The target 18 is specially adapted to enable the measurement of all three of the parameters absorption, reflection, and fluorescence, rendering the device 10 a "multi-parameter" device. The measurement of multiple parameters in the same device has a number of advantages. For example, the device is relatively simple and inexpensive as compared to employing a number of more specialized devices optimized for measuring particular parameters; signals for all measurements travel the same optical paths and employ the same source and detector, simplifying the monitoring of long-term drift in the device and facilitating corrections for drift in all measurements; and signal ratios are more constant because instrument artifacts are cancelled out. All of these features are enabled by the target 18.

The target 18 comprises a ball lens 22a and a cradle 22b. The cradle 22b serves to support the ball lens and acts as a partially focusing reflector. The ball lens serves to focus light received from the end 16a, and to further focus light reflected back to the end 16a by the cradle. In both cases, the light travels along a line "L."

It is believed to be important that the ball lens is substantially spherical, i.e., at least to within 5% and preferably at least to within 1%, and it will be readily appreciated that the ball lens should be substantially optically clear at the measuring frequencies of interest. Preferably, the ball lens is formed of fused silica because it has a broad transmission spectrum, particularly for transmitting ultraviolet light ("UV") down to a wavelength of less than about 200 nm, which is useful for probing, e.g., nitrates which are typically measured at a wavelength of 220 nm. However, the ball lens may be formed of other suitable materials.

The diameter of the ball lens 22a in the preferred embodiment shown is about 18 mm and the midpoint of the lens is preferably positioned such that outer-most rays of light exiting the end 16a and spreading about 22.5° encounter the lens about 1.0 mm from the edges thereof, to minimize optical aberrations that would result at the edges.

The cradle 22b includes a hemispherical or partially hemispherical (hereinafter "hemispherical") receptacle 23 shaped and sized to intimately receive the ball lens within close tolerance, and the interface between the ball lens and the cradle is preferably sealed against the seepage of water therebetween, such as by use of an O-ring 24. The hemispherical receptacle 23 serves to reflect and partially focus light passing through the ball lens.

The receptacle 23 is preferably oriented so that a rotational axis of symmetry "S" of the receptacle is coincident with the aforementioned line L of travel of the light.

It is recognized by the present inventor that the amount of light returned to the end 16a by the target 18 should be balanced between competing objectives. That is, a larger quantity of reflected light is better for measuring absorption, for comparing the light returned with the light emitted, while on the other hand, this makes it more difficult to measure fluorescence and reflection because a high degree of reflection produces scattered light and tends to reduce the signal to noise ratio. It has been found that forming at least the surface of the receptacle 23 of the cradle 22b of a material that absorbs, more than it reflects, light that is, nevertheless, polished sufficiently to reflect, more than it scatters, light at the wavelengths of interest, provides a good balance between these competing objectives. In the preferred embodiment shown, the entire cradle is formed of black plastic acetyl resin, such as that marketed as Delrin®, and the surface of the receptacle 23 is polished accordingly.

The ball lens 22a provides an additional feature of minimizing the effect of fouling, e.g., by algae, that occurs during use of the device 10 in monitoring water incoming to a municipal treatment plant, or water in a river, or in the ocean, such that the target will tend to lose its effectiveness to return light back to the end 16a. The convex, hemispherical shape of the portion of the ball lens exposed to fouling ensures that backscatter directly back to the end 16a remains relatively low.

As mentioned above, while somewhat reflective to enable absorption measurements, the target 18 is sufficiently dark to enable fluorescence and reflectance measurements. It is believed to be important in practice, though not essential in principle, that the target is resistant to UV damage that may be caused by the source 12. Therefore, the materials of which the target 18 is formed are preferably either inherently UV stable, such as the preferred fused silica for use in the ball lens 22a, or are treated to make them UV stable, such as the preferred acetyl resin for use in the cradle 22b.

The chamber 20 also houses an inner flow tube 26 which in turn houses the target 18. The inner flow tube 26 includes one or more apertures 25a, at a first end 26a of the tube through which water in the device 10 enters the tube, and one or more apertures 25b at a second end 26b of the tube through which the water exits the tube. In the preferred embodiment shown, the apertures 25a are a series of drilled holes set at an angle inclined toward the direction of water flow, while the apertures 25b are providing by spacing the end 26b of the tube 2 mm from the block 19.

The inner flow tube has an interior surface 27 that is relatively smooth as compared to the interior surface 21 of the chamber 20, which helps to maintain laminar flow around the target 18, to reduce the potential for forming bubbles that would interfere with the optical path of the light. In the preferred embodiment shown, the inner flow tube is formed of polyethylene terephthalate ("PET-P"), such as that marketed as Ertalyte®, chosen for its chemical inertness and low water permeability.

It is to be understood that, while a specific light returning target for a photometer has been shown and described as preferred, other configurations and methods could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A light returning target for a photometer, comprising:
   a substantially spherical ball lens; and
   a cradle having a matchingly hemispherical receptacle in which said lens is intimately received, said receptacle having a reflective surface for reflecting light passing through said lens.

2. The target of claim 1, wherein said lens is formed of fused silica.

3. The target of claim 2, wherein said surface is polished sufficiently to reflect, more than it scatters, light.

4. The target of claim 2, wherein said receptacle absorbs, more than it reflects, light.

5. The target of claim 4, wherein said surface is polished sufficiently to reflect, more than it scatters, light.

6. The target of claim 1, wherein said receptacle absorbs, more than it reflects, light.

7. The target of claim 6, wherein said surface is polished sufficiently to reflect, more than it scatters, light.

8. A photometer, comprising:
   a light source which emits light along a line; and
   a target, the target comprising a substantially spherical ball lens and a cradle having a matchingly hemispherical receptacle in which said lens is intimately received, said cradle being oriented so that said lens and said cradle together return at least a portion of the light along said line.

9. The photometer of claim 8, further comprising a chamber, a light detector, and a light pipe set including a bifurcated optical fiber for conducting the light from said light source and emitting the light into said chamber along said line, and for conducting the light returned along said line from said chamber to said light detector, said target being disposed inside said chamber.

10. The photometer of claim 9, wherein said chamber has an interior surface and further comprising a flow tube having one or more fluid inlets and one or more fluid outlets providing for fluid flow through said flow tube, said target being disposed within said flow tube, said flow tube having an interior surface that is smooth relative to said interior surface of said chamber, to help maintain laminar flow around said target.

11. The photometer of claim 9, wherein said lens is formed of fused silica.

12. The photometer of claim 11, wherein the surface of said receptacle is polished sufficiently to reflect, more than it scatters, the light.

13. The photometer of claim 12, wherein said receptacle absorbs, more than it reflects, the light.

14. The photometer of claim 11, wherein said receptacle absorbs, more than it reflects, the light.

15. The photometer of claim 8, wherein said lens is formed of fused silica.

16. The photometer of claim 15, wherein the surface of said receptacle is polished sufficiently to reflect, more than it scatters, the light.

17. The photometer of claim 15, wherein said receptacle absorbs, more than it reflects, the light.

18. The photometer of claim 17, wherein the surface of said receptacle is polished sufficiently to reflect, more than it scatters, the light.

19. The photometer of claim 8, wherein said receptacle absorbs, more than it reflects, the light.

20. The photometer of claim 19, wherein the surface of said receptacle is polished sufficiently to reflect, more than it scatters, the light.

21. A photometer, comprising:
a light source, wherein light emitted from said light source is made available as an output at a predetermined first point; and
a target, the target comprising a substantially spherical ball lens and a cradle having a matchingly hemispherical receptacle in which said lens is intimately received, said cradle being oriented so as to at least partially focus light received from said first point at a predetermined second point.

22. The photometer of claim 21, further comprising a light detector and a light pipe set including a bifurcated optical fiber for coupling light emitted from said light source to said first point, and coupling light focused at said second point to said light detector.

23. The photometer of claim 22, further comprising a chamber in which said target is disposed, wherein said chamber has an interior surface and further comprising a flow tube having one or more fluid inlets and one or more fluid outlets providing for fluid flow through said flow tube, said target being disposed within said flow tube, said flow tube having an interior surface that is smooth relative to said interior surface of said chamber, to help maintain laminar flow around said target.

24. The photometer of claim 22, wherein said lens is formed of fused silica.

25. The photometer of claim 24, wherein the surface of said receptacle is polished sufficiently to reflect, more than it scatters, light received thereby.

26. The photometer of claim 25, wherein said receptacle absorbs, more than it reflects, light received thereby.

27. The photometer of claim 24, wherein said receptacle absorbs, more than it reflects, light received thereby.

28. The photometer of claim 21, wherein said lens is formed of fused silica.

29. The photometer of claim 28, wherein the surface of said receptacle is polished sufficiently to reflect, more than it scatters, light received thereby.

30. The photometer of claim 28, wherein said receptacle absorbs, more than it reflects, light received thereby.

31. The photometer of claim 30, wherein the surface of said receptacle is polished sufficiently to reflect, more than it scatters, light received thereby.

32. The photometer of claim 21, wherein said receptacle absorbs, more than it reflects, light received thereby.

33. The photometer of claim 32, wherein the surface of said receptacle is polished sufficiently to reflect, more than it scatters, the light.

* * * * *